United States Patent [19]

Hegedus

[11] 4,400,973
[45] Aug. 30, 1983

[54] EFFLUX VISCOSITY CUP

[75] Inventor: Allan J. Hegedus, Bolingbrook, Ill.

[73] Assignee: Mobil Oil Corporation, New York, N.Y.

[21] Appl. No.: 327,547

[22] Filed: Dec. 4, 1981

[51] Int. Cl.³ .......................................... G01N 11/04
[52] U.S. Cl. ............................................. 73/56; 73/55
[58] Field of Search ..................................... 73/56, 55

[56] References Cited

U.S. PATENT DOCUMENTS

| 2,141,329 | 12/1938 | Zahn | 73/56 |
| 2,564,892 | 8/1951 | Gerin | 73/56 |
| 2,836,975 | 6/1958 | Euverard | 73/55 |
| 3,526,126 | 9/1970 | Wilchinsky et al. | 73/56 |

FOREIGN PATENT DOCUMENTS

| 386136 | 4/1965 | Switzerland | 73/56 |
| 169204 | 9/1921 | United Kingdom | 73/56 |
| 565232 | 7/1977 | U.S.S.R. | 73/55 |

OTHER PUBLICATIONS

A New Capillary Viscometer; by Greenwood, N. N. et al., in Journal of Scientific Instruments, vol. 34, Jul. 1957, p. 288.

Primary Examiner—Anthony V. Ciarlante
Assistant Examiner—David V. Carlson
Attorney, Agent, or Firm—Alexander J. McKillop; Michael G. Gilman; Charles J. Speciale

[57] ABSTRACT

This invention provides a rugged dip-type viscometer suitable for use in a rotogravure printing plant, for example. The capillary of the viscometer is joined to a slotted protective collar and gives high precision measurements with inks that contain air.

4 Claims, 11 Drawing Figures

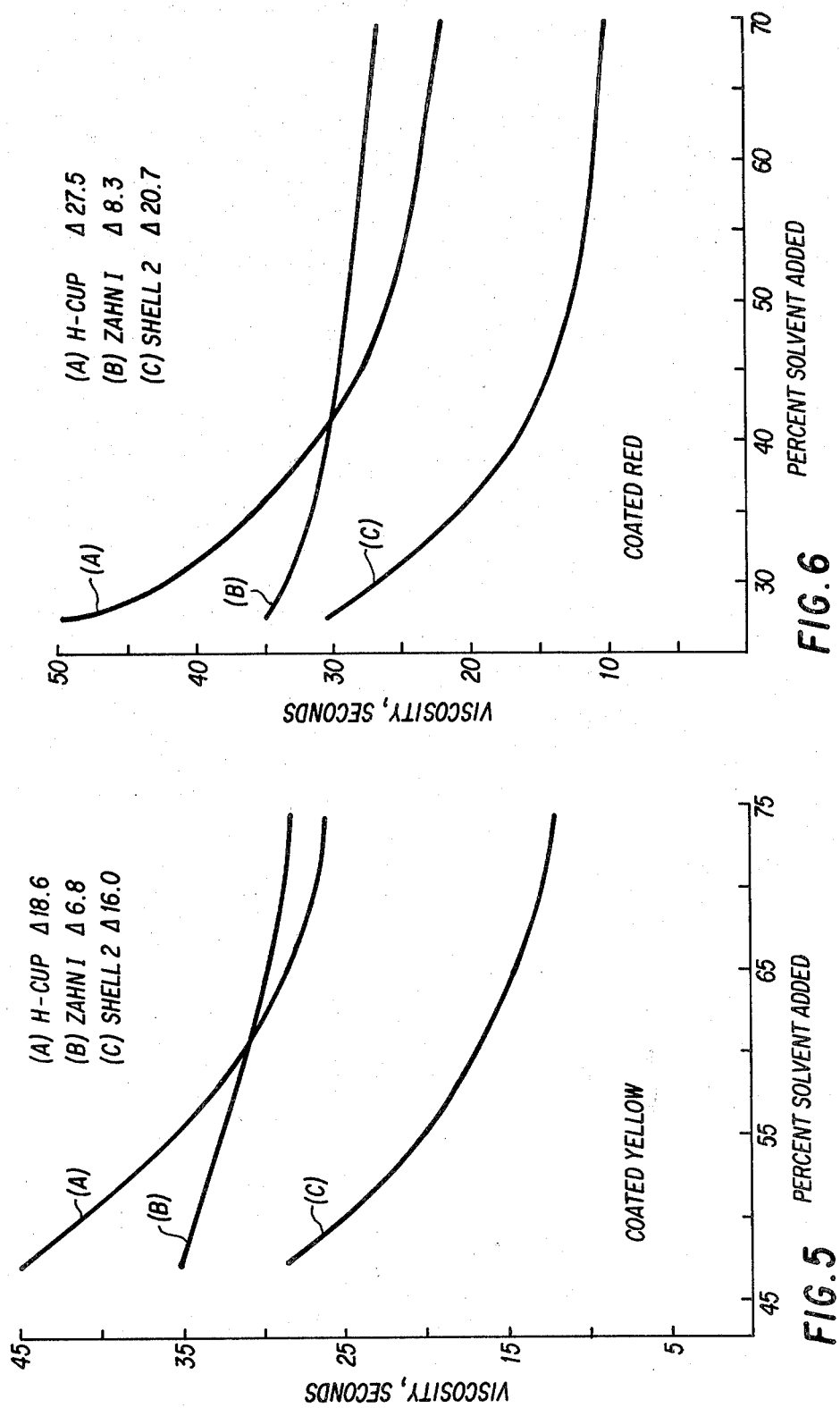

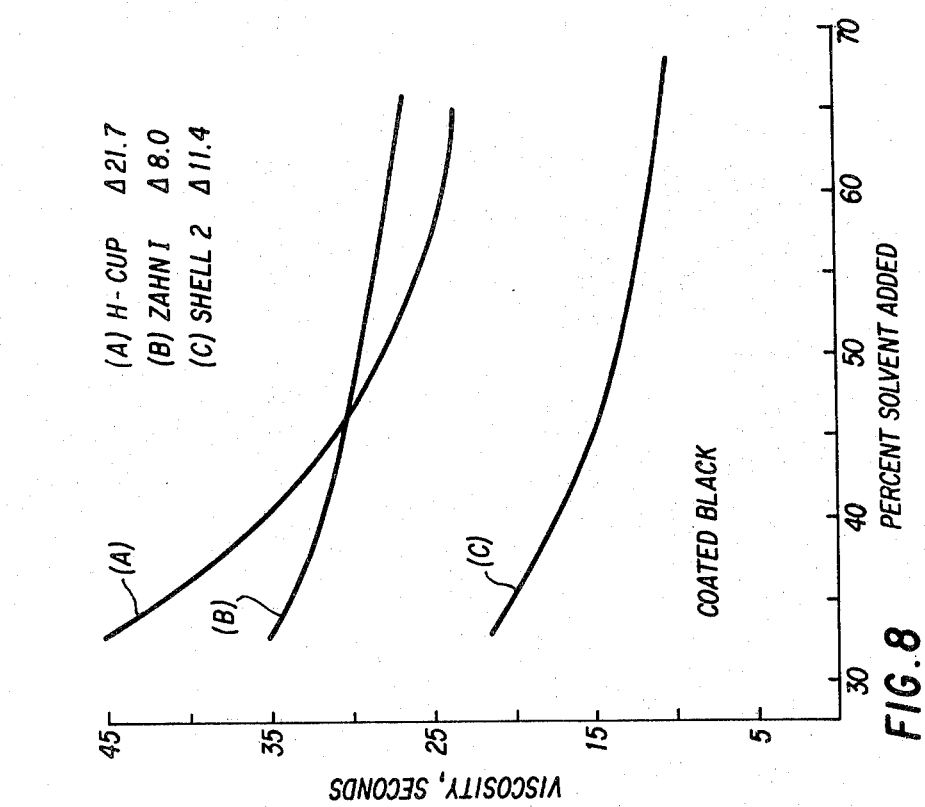
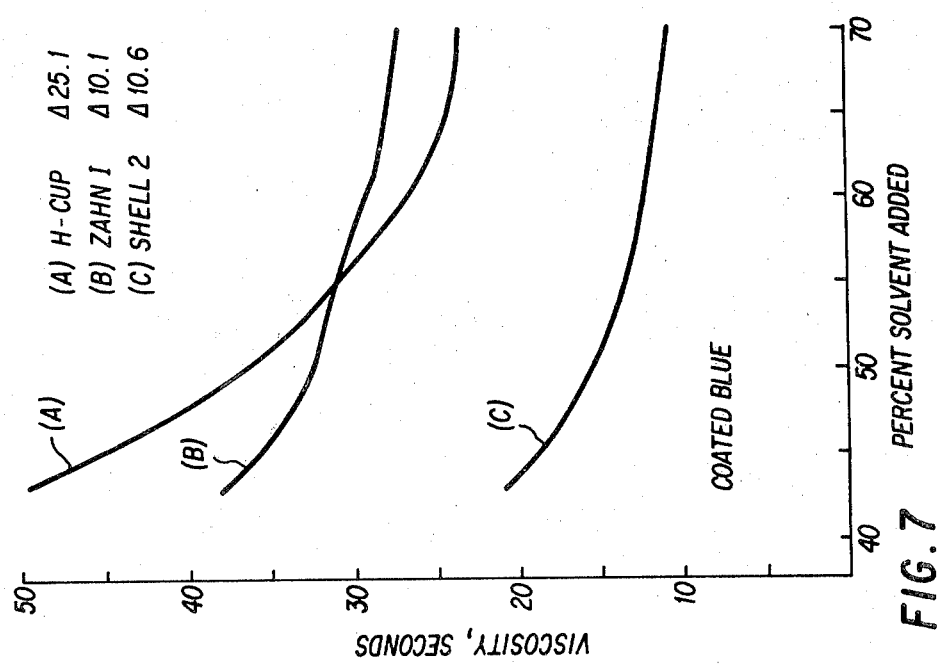

EFFLUX VISCOSITY CUP

BACKGROUND OF THE INVENTION

1. Field of the Invention

This invention is concerned with an improved dip-type efflux viscosity cup. The improved cup is particularly useful for controlling the viscosity of rotogravure printing inks in the pressroom and for checking the calibration of automatic viscosity controls.

2. Prior Art

A large number of viscometers have been proposed and are in use for measuring the viscosity of paints, varnishes, lacquers, gravure and flexographis printing inks, and of other fluid products such as adhesives and petroleum oils. A relatively inexpensive and relatively durable type of viscometer which is well adapted to plant use is the dip-type efflux cup, exemplified by the well known Zahn cup, and the equally well known Shell cup. The Zahn cup is described, for example, on page 1349 of the Sargent-Welch Catalog of Scientific Laboratory Instruments, and on page 1271 of the 1981 Fisher Scientific Catalog. This cup consists essentially of a cylindrical cup with a hemispherical bottom and has a nominal volume of about 44 ml and, concentric with the cylindrical axis, an orifice which varies from about 80 to about 210 thousands of an inch, permitting a range of measurement of about 14 to about 13 hundred centipoises. The cup is provided with a long, looped handle and holding ring and it may be provided also with a thermometer. One of the disadvantages of the cup is that the orifice generally has no protection from accidental mechanical damage, for example, and therefore is subject to change in calibration.

In use, the Zahn cup is chosen having an orifice such that the liquid to be tested has an efflux time of less than about one minute. The cup is immersed into the liquid to be tested, and the viscosity is measured by raising the cup out of the liquid and determining the length of time required for the stream to break.

The Shell cup is similar to the Zahn cup except that it utilizes a capillary tube normally protected by a lip and constructed integrally with the body of the cup. It is altogether somewhat more rugged, but the protecting lip may result in the entrapment of dirt or minute air bubbles and cause distortion of the flow pattern from the capillary and create reproducibility problems.

A modification of the Shell cup, which will be referred to herein as the "S cup", provides a protective collar around the orifice which extends about 2 (two) mm beyond the orifice of the capillary. With the S-cup, the orifice has the same diameter as the capillary itself, i.e., there is no lip around the orifice. Unlike the usual Shell and Zahn cups, the S-cup is free-standing and may be stored on a shelf or table without damage to the exit orifice of the capillary.

The present invention was motivated by repeated complaints from the pressroom of a rotogravure plant concerning the inability to achieve good light end point-out and maintain solid color density.

It is known that one of the most vital characteristics of a gravure ink, with respect to its performance, is the viscosity at which it is printed. Optimum press viscosity insures consistent quality results in the areas of printability, trapping efficiency, level of gloss, adhesion, color density and drying speed—to mention a few of the most important. Experience in the pressroom indicated that good printability on a coated stock red can be achieved by maintaining the viscosity of the ink between 29 and 28 seconds on a Zahn-1 cup.

A preliminary study of the viscosity control problem indicated that the Zahn cup lacked adequate sensitivity for good control. The S-cup, which is a modified Shell cup, appeared best suited in design and in sensitivity to measure the viscosity of rotogravure inks in the region in question. However, it was noted that the S-cup suffered from excessive scatter of data points.

It is an object of this invention to provide an improved efflux viscosity cup which is rugged in design, well adapted to routine production control in a plant environment, and which offers a combination of good sensitivity and good repeatability from test to test.

SUMMARY OF THE INVENTION

The efflux viscosity cup of this invention designated herein as the "H-cup", is of basically the same design and dimensions as the S-cup of the prior art except for the provision of a pair of slots or arches cut in the protective collar with the top of the slot located at or slightly above the land bridging the capillary and the collar.

BRIEF DESCRIPTION OF THE DRAWINGS

FIG. 5—Comparisons with Coated Yellow

FIG. 6—Comparisons with Coated Red

FIG. 7—Comparisons with Coated Blue

FIG. 8—Comparisons with Coated Black

DETAILED DESCRIPTION

Figure 1:
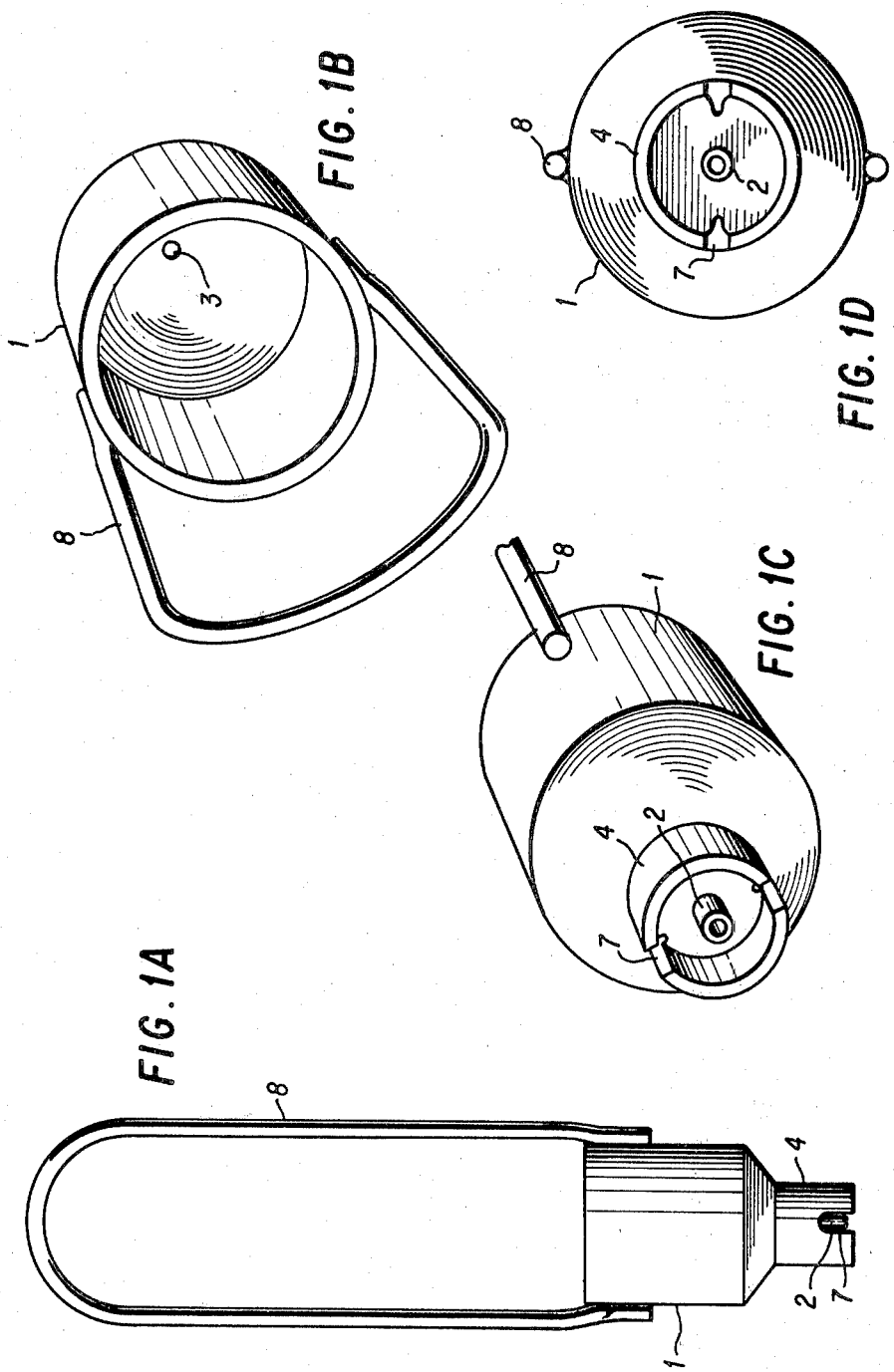
FIGS. 1A, 1B, 1C and 1D—Perspective views of H-cup

FIGS. 1A, 1B, 1C and 1D of the drawing show several perspective views of the H-cup.

Figure 2:
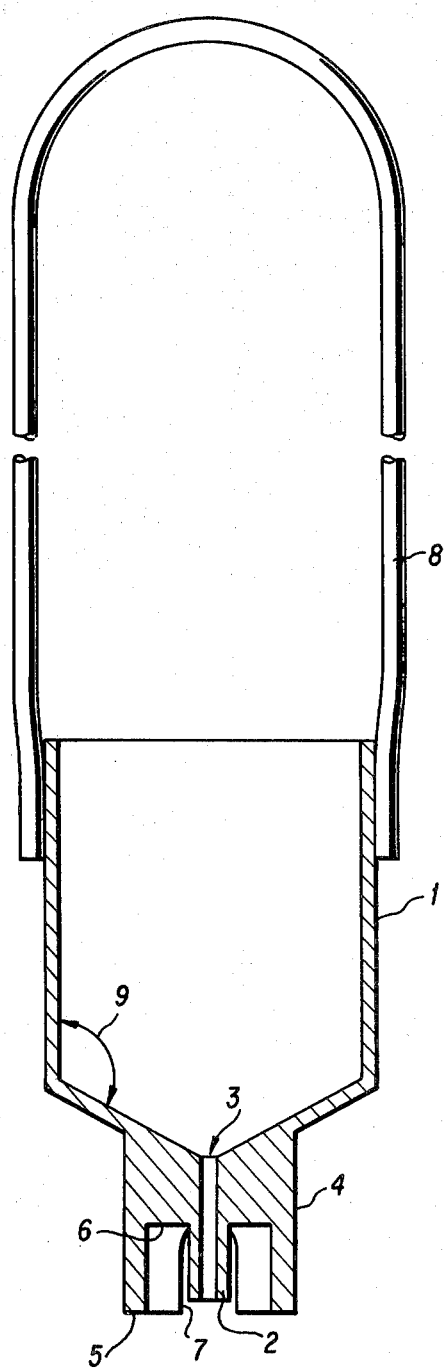
FIG. 2—Cross section of H-cup

FIG. 2 of the drawing shows a cross-section of the H-cup and illustrates the overall unitized construction which is the preferred embodiment for purposes of this invention. The entire structure preferably is formed from a single block of stainless steel except for the handle which may be welded to the cup. The cylindrical cup with a conical bottom (1) joined to capillary (2) at the apex of the cup constitutes the basic viscometer. With unitized construction, the bore (3) of the capillary is initally made undersized, the cup tested, and then the capillary is rebored to exact size. The protective collar (4) is machined such that its inner diameter is about ⅜ inch to about one inch larger than the outer diameter of the capillary (2) and extends beyond the end of the capillary about 2 millimeters, thus protecting the capillary from mechanical damage and providing a base (5) for free-standing storage. The collar (4) is joined to the capillary (2) by a land (6) which is essentially parallel with the plane of the base (5). One or preferably two slots (7) extending from the base (5) at least to the land (6) are provided in collar (4). The slots may take the form of arches, as shown. The slots or arches have a width of about ⅛ inch to ¼ inch. The angle (9) at the junction of the cone and cylinder may vary, but preferably is in the range of about 120° to about 140°. While not wishing to be bound by theory, it is believed that the slots improve reproducibility by facilitating the disengagement of air. The cup if fitted with handle (8).

Figure 3:
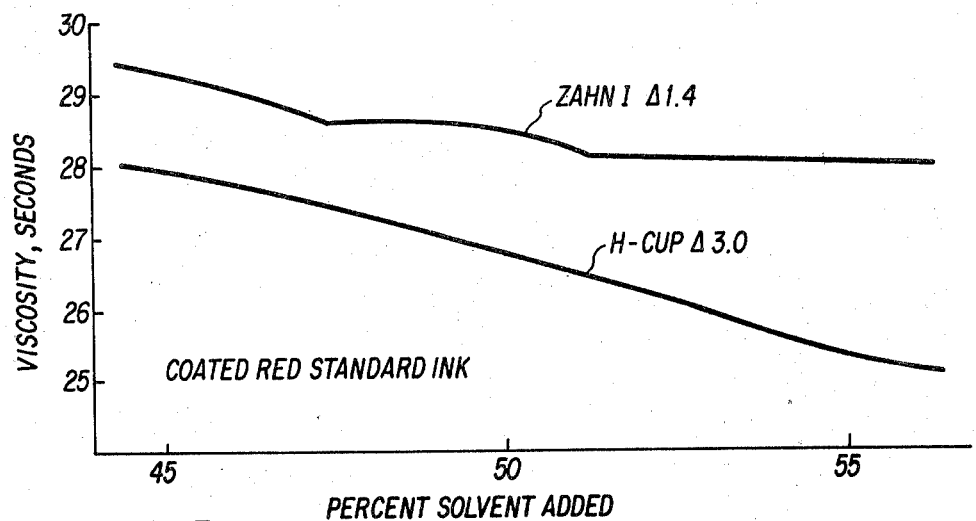
FIG. 3—Comparison of Zahn and H-cup

FIG. 3 illustrates the reduction of viscosity as measured by the Zahn-1 cup as a rotogravure ink is let down into the region of 28-29.4 seconds Zahn-1 viscosity. In this instance and all others shown herein, the percent solvent added is computed from:

$$\frac{\text{milliliters of solvent}}{\text{grams of ink + milliliters of solvent}} \times 100$$

It will be noted that the sensitivity of the Zahn cup falls off rapidly after an addition of about 47.5% solvent. The designation "coated red standard ink", etc., means a standard red for coated stock.

Figure 4:
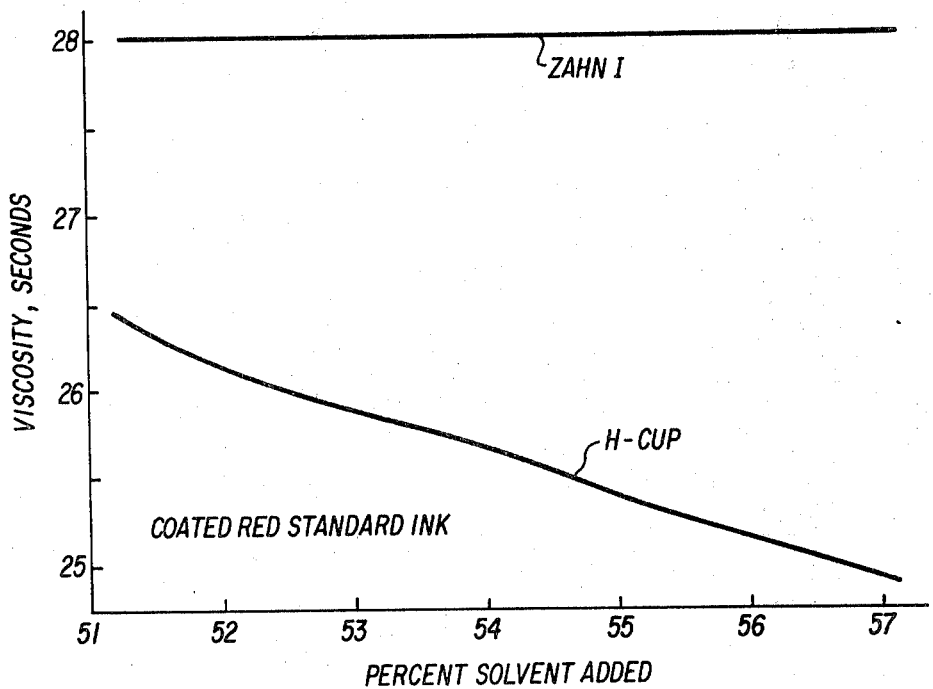
FIG. 4—Comparison of Zahn and H-cup

FIG. 4 compares the behavior of the Zahn-1 viscosity with the H-cup behavior over the region covered by the addition of 51-57% solvent. It is noteworthy that the Zahn cup is completely insensitive in this region giving a viscosity of about 28 seconds regardless of the dilution, whereas the H-cup responds with a change of about 1.5 seconds over the range.

FIGS. 5, 6, 7 and 8 illustrate the comparative behavior of the H-cup, the Zahn-1 and the Shell-2 for dilution of a set of gravure inks for application on coated stocks. In all cases, the H-cup maintains its sensitivity over a wide range of dilutions, and the Zahn cup is much less sensitive. The Shell cup is reasonably sensitive, as would be expected from its capillary element, but in all cases the H-cup gives the largest total differences from the lowest to the highest dilutions.

The physical characteristics and measurements of the cups used in the above tests are given in Table I. The somewhat larger capillary compared with the Shell cup reduces the chance for error from small particles of dirt.

TABLE I

PHYSICAL CHARACTERISTICS AND APPROXIMATE MEASUREMENTS

|  | H-CUP | S-CUP | ZAHN-1 | SHELL-2 |
|---|---|---|---|---|
| Weight (g.) | 318.5 | 274 | 103 | 144 |
| Volume (ml) 75° F. | 110 | 110 | 46 | 23 |
| Capillary Length (mm) | 21 | 21 | 0 | 25 |
| Orifice Diameter (mm) | 3 | 3 | 1.5 | 2 |

Table II shows the viscosity of different pure liquids in the four cups referred to.

TABLE II

VISCOSITIES OF DIFFERENT PURE SOLVENTS (Seconds)

|  | H-CUP | S-CUP | ZAHN-1 | SHELL-2 |
|---|---|---|---|---|
| Xylene 72° F. | 20.7 | 20.5 | 27.2 | 8.6 |
| Water 72° F. | 22.0 | 22.2 | — | 10.0 |
| Rotosolv 2271 72° F. | 21.5 | 21.0 | 28.0 | 8.5 |

Table III shows the variations of viscosity of a red rotogravure ink as temperatures change with the four cups under study.

TABLE III

VISCOSITIES (Secs.) AT VARYING TEMPERATURES, RED GRAVURE INK

| TEMPERATURE | H-CUP | S-CUP | ZAHN-1 | SHELL-2 |
|---|---|---|---|---|
| 42° F. | 45.2 | 45.0 | 33.8 | 27.5 |
| 72° F. | 35.7 | 35.0 | 31.0 | 19.4 |
| 104° F. | 30.0 | 30.0 | 29.3 | 15.0 |

As would be expected from the similarity of construction and of dimensions, the foregoing tables reflect similar behavior for the S-cup of the prior art and the H-cup of this invention. However, a statistical study of repeatability based on 50 tests with each the S-cup and the H-cup showed a radical difference in precision. A blend of mineral seal oils free of solvent and having a viscosity of 10 centipoises was used for these tests. The results of these tests, shown in Table IV, illustrates a marked superiority of the H-cup as compared with the S-cup.

TABLE IV

| REPEATABILITY | | |
|---|---|---|
|  | H-CUP | S-CUP |
| Value of Mean | 32.48 | 31.65 |
| Standard Deviation | 0.102 | 0.313 |

While the present invention has been described with particular attention given to the application of the improved cup of this invention to the measurement of the viscosity of gravure ink in a printing plant environment, it will be recognized that the advantages provided will be equally applicable to the measurement of paints, lacquers, and other liquids which require monitoring of viscosity under adverse conditions. Also, whereas the present cup has been described in a form suitable for measuring the viscosity of liquids in the range of those that would be measured by a Shell-2 cup, it is well evident that a set of cups with applicability over a range of viscosity comparable with different Shell cups is provided simply by changing the size of the capillary bore.

What is claimed is:

1. In an efflux viscosity cup consisting essentially of a cylindrical cup with a conical bottom, a capillary joined to the apex of said conical bottom which apex is provided with an orifice, said cylindrical cup, conical bottom and capillary being coaxially oriented with one another, and a coaxially oriented cylindrical protective collar having an inner diameter substantially larger than the outer diameter of said capillary and attached thereto by a land located at about the midpoint along the length of the capillary, said collar extending beyond the exit orifice of the capillary by about two millimeters, the improvement whereby increasing the reproducibility of measurements made with said cup, which comprises including in said collar a slot with sides perpendicular to the base of the collar and extending from the base at least to the land.

2. The article described in claim 1 wherein two said slots are included in said collar.

3. The article described in claim 1 or claim 2 wherein said slots are arches.

4. The article described in claim 2 having a volume of about 110 ml and a capillary length of about 21 millimeters.

* * * * *